United States Patent
Maaskamp et al.

(10) Patent No.: US 11,191,666 B2
(45) Date of Patent: Dec. 7, 2021

(54) RECTOCELE GUIDE SHEATH

(71) Applicants: Ryan Maaskamp, Scottsdale, AZ (US);
Armand Maaskamp, Scottsdale, AZ (US)

(72) Inventors: Ryan Maaskamp, Scottsdale, AZ (US);
Armand Maaskamp, Scottsdale, AZ (US)

(*) Notice: Subject to any disclaimer, the term of this patent is extended or adjusted under 35 U.S.C. 154(b) by 0 days.

(21) Appl. No.: 17/177,118

(22) Filed: Feb. 16, 2021

(65) Prior Publication Data

US 2021/0161702 A1    Jun. 3, 2021

Related U.S. Application Data

(62) Division of application No. 16/582,904, filed on Sep. 25, 2019.

(51) Int. Cl.
| | |
|---|---|
| *A61F 6/12* | (2006.01) |
| *A61B 1/00* | (2006.01) |
| *A61F 5/00* | (2006.01) |
| *A61M 29/02* | (2006.01) |

(52) U.S. Cl.
CPC ............ *A61F 6/12* (2013.01); *A61B 1/00142* (2013.01); *A61F 5/0093* (2013.01); *A61M 29/02* (2013.01); *A61B 1/00131* (2013.01)

(58) Field of Classification Search
CPC ... A61B 1/00142; A61B 1/00131; A61F 6/12; A61F 5/0093; A61M 29/02
USPC ..................................................... 600/29–32
See application file for complete search history.

(56) References Cited

U.S. PATENT DOCUMENTS

| | | | |
|---|---|---|---|
| 860,591 | A | 7/1907 | Baird |
| 2,400,251 | A | 5/1946 | Nagel |
| 2,494,393 | A | 1/1950 | Lamson |
| 2,856,920 | A | 10/1958 | Indelicato |
| 3,994,291 | A | 11/1976 | Salmasian |
| 4,612,924 | A | 9/1986 | Cimber |
| 4,669,478 | A | 6/1987 | Robertson |
| 4,875,898 | A | 10/1989 | Eakin |
| 4,920,986 | A | 5/1990 | Biswas |
| 4,986,823 | A | 1/1991 | Anderson |
| 5,364,146 | A | 11/1994 | Brandorff |

(Continued)

FOREIGN PATENT DOCUMENTS

| | | |
|---|---|---|
| EP | 0700669 A1 | 3/1996 |
| FR | 2228464 83 | 4/1976 |

*Primary Examiner* — Navin Natnithithadha
*Assistant Examiner* — Sunita Reddy
(74) *Attorney, Agent, or Firm* — Kenneth Altshuler (57) ABSTRACT

A rectocele device having an inflatable balloon and extendable armature inside of the balloon as the balloon expands provides added stability when used to push on a rectocele. More specifically, a rectocele handle can include a rectocele paddle, which can extend in length, and balloon combination extending from the handle. A protective sheath that has a tubular body covers the balloon. The paddle, generally comprised by a piston and piston housing, can increase its length by way of a piston extending in and out of the piston housing. When the rectocele paddle and balloon combination is deployed in a vagina, to push on the rectocele, the balloon is inflated which causes the piston to extend from the piston housing with the balloon inflation. The piston and piston housing paddle provide stability for the inflated balloon.

19 Claims, 9 Drawing Sheets

(56) References Cited

U.S. PATENT DOCUMENTS

| | | |
|---|---|---|
| 5,603,685 A | 2/1997 | Tutrone, Jr. |
| 5,716,329 A | 2/1998 | Dieter |
| 5,988,169 A | 11/1999 | Anderson |
| 6,077,257 A | 6/2000 | Edwards |
| 6,168,586 B1 | 1/2001 | Hahnen |
| 6,468,232 B1 * | 10/2002 | Ashton-Miller ....... A61B 5/227 600/591 |
| 6,676,594 B1 | 1/2004 | Zunker |
| 6,795,737 B2 | 9/2004 | Gielen |
| 7,179,219 B2 | 2/2007 | Matlock |
| 7,288,063 B2 | 10/2007 | Petros |
| 7,325,546 B2 | 2/2008 | Burbank |
| 7,513,868 B1 | 4/2009 | Fontenot |
| 7,634,049 B2 | 12/2009 | Galkin |
| 7,771,344 B2 | 8/2010 | Ziv |
| 7,981,024 B2 | 7/2011 | Levy |
| 8,302,608 B2 | 11/2012 | Harmanli |
| 8,360,954 B2 | 1/2013 | Kim |
| 2003/0078526 A1 | 4/2003 | Farley |
| 2005/0021080 A1 | 1/2005 | Feuer et al. |
| 2006/0025782 A1 | 2/2006 | Klein et al. |
| 2006/0211911 A1 | 9/2006 | Jao et al. |
| 2009/0216071 A1 | 2/2009 | Zipper |
| 2009/0266367 A1 * | 10/2009 | Ziv .......................... A61F 2/005 128/834 |
| 2010/0174214 A1 | 7/2010 | Gabbay et al. |
| 2014/0243584 A1 * | 8/2014 | Bercovich ................ A61F 6/08 600/29 |
| 2014/0261445 A1 * | 9/2014 | Maaskamp ............... A61F 6/12 128/835 |
| 2014/0275749 A1 * | 9/2014 | Maaskamp ........... A61F 2/0027 600/37 |
| 2016/0022400 A1 * | 1/2016 | Alexander ............... A61B 1/06 600/37 |
| 2016/0331407 A1 * | 11/2016 | Anderson ............... A61B 17/42 606/144 |
| 2017/0100278 A1 * | 4/2017 | Ziv .......................... A61F 6/12 |
| 2018/0256389 A1 * | 9/2018 | Asfar ........................ A61F 6/08 |
| 2020/0253817 A1 * | 8/2020 | Do Coutto ............. A61H 19/40 |

\* cited by examiner

RECTOCELE GUIDE SHEATH

CROSS-REFERENCE TO RELATED APPLICATIONS

This application is a divisional application of U.S. Ser. No. 16/582,904, entitled Rectocele Guide filed on Sep. 25, 2019.

FIELD OF THE INVENTION

The present invention is directed to a rectocele device that is useful in reducing the effects of rectoceles in women.

BACKGROUND OF THE INVENTION

Figure 1:
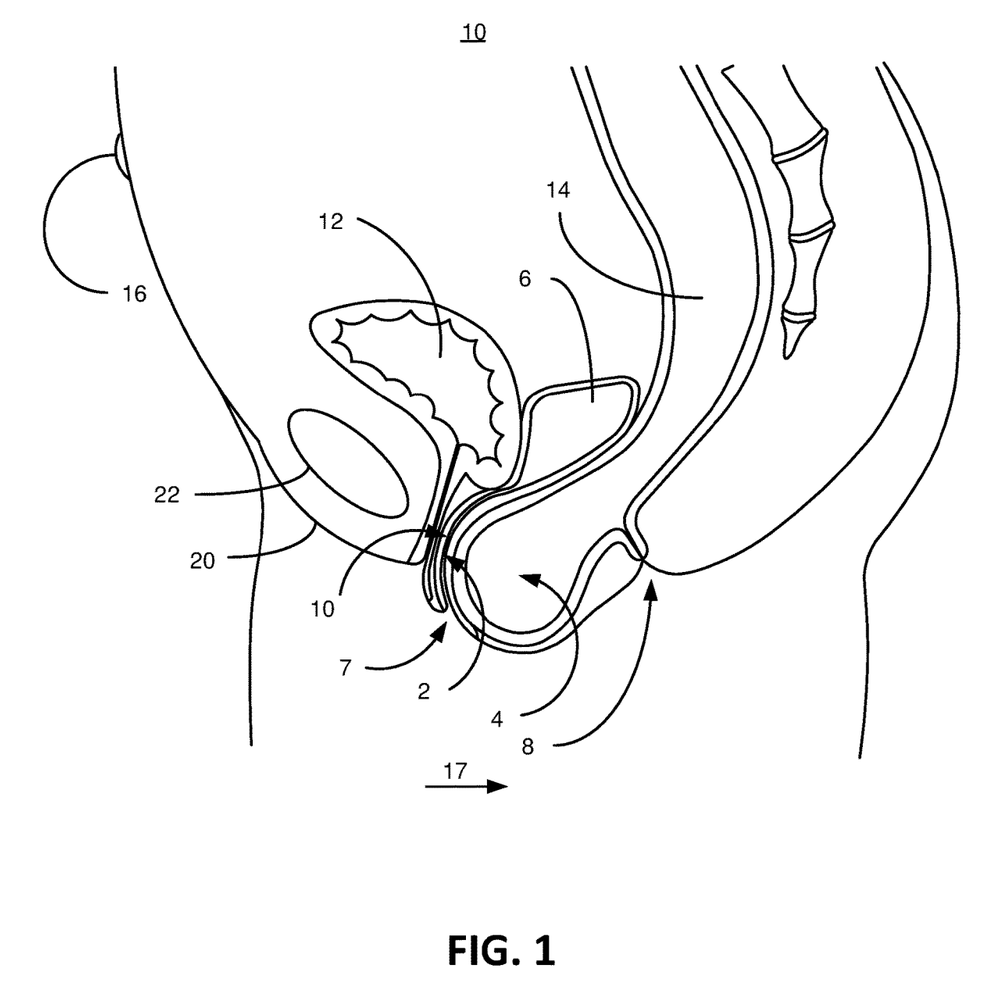
FIG. 1 depicts a cross section of a pelvic area of a woman suffering from a rectocele.

A rectocele is a herniation (bulge) of the front wall of the rectum into the back wall of the vagina. The tissue between the rectum and the vagina is known as the rectovaginal septum and this structure can become thin and weak over time, resulting in a rectocele. When rectoceles are small, most women have no symptoms. However, when a rectocele becomes large, a woman's rectum can balloon into her vagina, which can be exacerbated during a bowel movement as shown in FIG. 1. As a result, the woman may experience the sensation of pressure or protrusion within the vagina, and the occasional feeling that the rectum has not been completely emptied after a bowel movement. In more moderate cases, a woman may have difficulty passing stool because the attempt to evacuate pushes the stool into the rectocele instead of out through the anus.

In an attempt to aid with a bowel movement in cases of rectocele, a woman may insert her fingers into her vagina to manually press against the rectocele which helps create a uniform pathway for stool to move out of the rectum. Because a rectocele may protrude to the right or left of the posterior wall of the vagina, by using the sense of touch in her fingers, a woman is able to reposition her fingers to where the rectocele occurs. In other words, a woman is able to press against the rectocele with her fingers by taking advantage of bio-feedback in her fingers.

Though surgical procedures exist to repair rectoceles and cystoceles, in less severe cases, a number of optional devices currently exist to provide some rectocele and/or cystocele relief. One family of devices includes spoon-like instruments, which are used to assist in a bowel movement just prior to having the bowel movement and then is withdrawn after the bowel movement. Unlike the biofeedback of fingers to facilitate repositioning of pressure against the rectocele or the cystocele, spoon-like devices are unable to sense if a rectocele or cystocele is sliding to the right or left of the spoon. In one example, when a rectocele slides to the right or left of the spoon, the woman may press harder against her posterior rectovaginal wall with the spoon because she is not experiencing proper stool evacuation and cannot sense through bio-feedback that the rectocele has moved around the spoon, which then may cause damage to her posterior rectovaginal wall. The same problem applies to a cystocele.

Another family of devices used to address rectoceles includes pessaries, which are typically inflated balloons that provide static pressure on all surfaces of the vaginal canal (the rectovaginal wall, lateral walls and the bladder-vaginal wall). Pessaries offer extended support to address rectoceles. Unlike a spoon for assisting in a bowel movement, pessaries are not inserted into a vagina just prior to a bowel movement to the point of when a bowel movement is complete or prior to the point of urination or just when urination is complete. Rather, pessaries are left in the vagina for an extended period of time, sometimes being inserted in the morning and removed at night or even to being left in for days at a time, if not longer. Moreover, due to the static nature of pessaries, pessaries are unable to be manipulated to push prolapsing organs back into place once inserted in a vagina.

It is to innovations related to addressing passing a bowel movement in women suffering from a rectocele that the claimed invention is generally directed.

SUMMARY OF THE INVENTION

The present invention is directed to a rectocele/cystocele device that is useful in providing pressure against the rectocele to improve bowel movements in women or against the cystocele to improve urination events in women.

One embodiments of the present invention can therefore comprise a rectocele device comprising: a rectocele handle defined in part between a proximal handle end and a distal handle end; a vaginal piston housing extending from the distal handle end and terminating at a piston housing distal end, a piston through port located at the vaginal piston housing distal end; a piston inside of the vaginal piston housing, the piston possessing a piston distal end, the piston distal end exposed at the piston through port, the piston inseparable from the vaginal piston housing; an uninterrupted unidirectional passageway extending through the rectocele handle from the proximal handle end through the distal handle end and into the vaginal piston housing; and at least one exit aperture extending through the vaginal piston housing, the at least one exit aperture in communication with the passageway.

Another embodiment of the present invention can therefore comprise a rectocele device comprising: a rectocele handle defined in part by a proximal handle end and a distal handle end; a vaginal piston housing attached to the distal handle end and terminating at a piston housing distal end, a piston through port located at the vaginal piston housing distal end; a piston that is at least in part confined inside of the vaginal piston housing, the piston possessing a piston distal end, a piston through port that accommodates movement of the piston, the vaginal piston housing and the piston 305 are inseparable components of a vaginal paddle; an uninterrupted unidirectional passageway extending through the rectocele handle from the proximal handle end through the distal handle end and into the vaginal piston housing; and a balloon essentially covering the vaginal piston housing, the balloon defined by an inside surface, an outside surface, a drip point and a balloon lip, the balloon lip defining an inflation outlet, the inside surface in communication with the passageway.

Yet another embodiment of the present invention can therefore comprise a rectocele device comprising: a vaginal piston housing possessing a proximal end configured to connect to a distal handle end of a rectocele handle that is defined in part by a proximal handle end and a distal handle end, the vaginal piston housing terminating at a piston housing distal end, a piston through port located at the vaginal piston housing distal end; a piston that when in a first position is substantially inside of the vaginal piston housing, the piston extended through the piston through port in a position beyond the first position when in a second position, the piston stays in cooperation with the vaginal piston housing in both the first and the second positions; an inlet port at the proximal end and at least one outlet port that passes through the vaginal piston housing; an uninterrupted unidirectional pathway between the inlet port and the outlet port; and the piston terminating at a piston distal end, the piston distal end adapted to confront a balloon interior.

DETAILED DESCRIPTION

Initially, this disclosure is by way of example only, not by limitation. Thus, although the instrumentalities described herein are for the convenience of explanation, shown and described with respect to exemplary embodiments and related examples, it will be appreciated that the principles herein may be applied to equally similar types of devices involving holding back rectoceles. The term example as used herein is synonymous with the term embodiments.

Aspects of the present invention are generally directed to a rectocele device having an inflatable balloon and extendable armature inside of the balloon as the balloon expands providing added stability when used to push on a rectocele. More specifically, a rectocele handle can include a rectocele paddle, which can extend in length, and balloon combination extending from the handle. The rectocele paddle, generally comprised by a piston and piston housing, can increase its length by way of a piston extending in and out of the piston housing. When the rectocele paddle and balloon combination is deployed in a vagina, to push on the rectocele, the balloon is inflated which causes the piston to extend from the piston housing with the balloon inflation. The piston and piston housing paddle provide stability for the inflated balloon.

Other aspects of the present invention contemplate a protective sheath covering the paddle and a portion of the handle to safeguard against bio-contamination.

FIG. 1 depicts a cross section of a pelvic area of a woman 10 suffering from a rectocele 4 thereby illustrating an exemplary environment in which embodiments of the present invention can be practiced. The rectocele 4 is shown bulging into the rectovaginal wall 2 of the vagina 6. The rectovaginal wall 2 is the septum between the vaginal vault (vagina) 6 and the rectal vault (rectum) 14 in the posterior direction 17 of the vagina 6. For reference, also shown herein, are the bladder 12, the bladder-vaginal wall 10, the vaginal opening 7, and the anus 8. Though not shown, the vagina 6 also has lateral walls of the vagina 6, which directionally extend towards the inner thighs of the woman 10. In other words, the rectovaginal wall 2 extends towards the posterior 17 and the bladder-vaginal wall extends towards the anterior (pubic bone 22) of the woman 10, whereas, the lateral walls of the vagina 6 are orthogonal to the anterior/posterior direction. From the anterior side, also shown are the belly button 16, the pubic bone 22, and the mons veneris 20.

Figure 2:
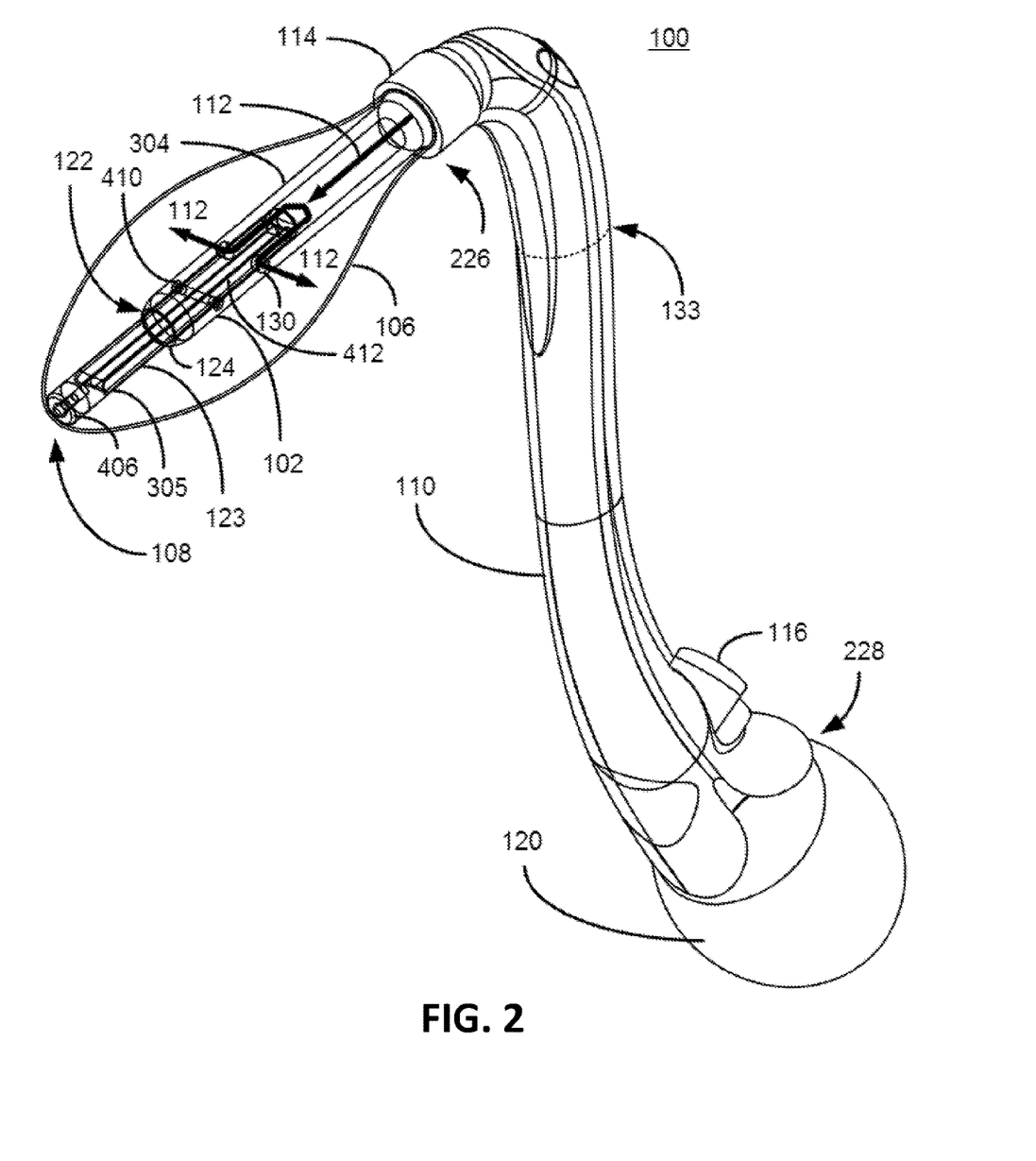
FIG. 2 illustratively depicts a line drawing of a rectocele device in operation consistent with embodiments of the present invention.

FIG. 2 illustratively depicts a line drawing of a rectocele device 100 in operation consistent with embodiments of the present invention. The main components shown include a rectocele handle 110, a paddle 102, a balloon 106 and a pressure bulb 120. With more specificity, the rectocele handle 110 is defined, or otherwise extends, between a proximal handle end 228 and a distal handle end 226. The word "defined" as used herein (i.e., "an element defined by") is not to be interpreted as exclusive, but rather is intended to be interpreted as inclusive. The paddle 102 generally comprises a vaginal piston housing 304 that extends from the distal handle end 226 and terminates at a piston housing distal end 122. The vaginal piston housing 304 is so called because it is sized and configured exclusively for a vagina 6.

In certain embodiments, the paddle 102 can be connected to the distal handle end 226 by way of a threaded fitting, a javelin fitting, a rib and cuff fitting, a clamp fitting, a set screw and cuff fitting, or some other fitting known to those skilled in the art. While in other embodiments, at least part of the paddle 102 is a unitary extension from the handle 110. The vaginal piston housing 304 (hereinafter "piston housing") is intended to be inserted and resides in a vagina 6 to assist in pushing on a rectocele 4. In some embodiments, the rectocele device 100 is inserted in a vagina 6 approximately up to the vagina entry location 133. In other words, a vaginal interior region is defined as between the paddle distal end 108 approximately up to the vagina entry location 133 when the rectocele device 100 is inserted in a vagina 6 during a bowel movement from between the paddle distal end 108 approximately up to the vagina entry location 133. The piston housing 304 can be, but is not limited to, a unitary material that possesses the fitting structure that interfaces with the housing distal end 122. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). The piston housing 304 houses a piston 305 that essentially resides inside of the piston housing 304. The piston housing 304 defines a piston through port 124 located at the piston housing distal end 122. The piston through port 124 is sized to accommodate axial movement of the piston 305 inside and out of the piston housing 304. The piston 305 is essentially defined by a piston shaft 123 terminating at a piston distal end 406. The piston distal end 406 is exposed at the piston through port 124. In certain embodiments the piston distal end 406 is partially extended through the piston through port 124, while other embodiments envision the piston distal end 406 essentially inside of the piston housing 304 but visibly exposed through the piston through port 124. In the embodiment shown, the piston through port 124 is entirely open to the piston distal end 406 with nothing covering or otherwise obstructing the piston distal end 406. In other words, in the present embodiment there is no flexible material to retain the piston 305 inside of the piston housing 304. The reason why there is nothing covering the piston distal end 406 in the depicted embodiment is because the piston distal end 406 is configured to interface, or otherwise confront, a balloon 106 as shown. The piston 305 moves axially in and out of the piston housing 304 as is standard movement of a piston. In the present embodiment, the piston 305 moves in and out of the piston housing 304 along axis 350.

In the present embodiment, the piston 305 is inseparable from the piston housing 304 by way of a pin 410 and slot 412 configuration. The term "inseparable" means that the piston 305 does not completely come out of the piston housing 304. Accordingly, in the present embodiment it is undesirable for the piston 305 to be independent from the piston housing 304. Other embodiments keeping the piston 305 from separating from the piston housing 304 can include a lip, a stop, or other separation prevention configurations known to those skilled in the art. One advantage of the pin 410 and slot 412 configuration is in preventing the piston 305 from rotating within the piston housing 304.

Also shown in FIG. 2, when the bulb 120 is squeezed by hand, pressurized air 112 flows through the handle 110, then through the piston housing 304 and out through the exit apertures 130 into the balloon 106. As the balloon 106 expands, the piston 305 extends axially out from the piston housing 304. Though the present embodiment depicts the piston 305 extending axially out from and through the center of the piston housing 304, other embodiments envision non-centric configurations. The balloon 106 expands and holds pressure because of the one-way valve 116 near the proximal end 228 of the handle 110. The one-way valve 116 is envisioned to be manually actuated to let the air out upon desiring to do so, thereby contracting the balloon 106 around the paddle 102 forcing the piston 305 to retract back inside of the piston housing 304. This process is done when a woman finishes her bowel movement and no longer needs an inflated paddle 102/balloon 106.

Figure 3:
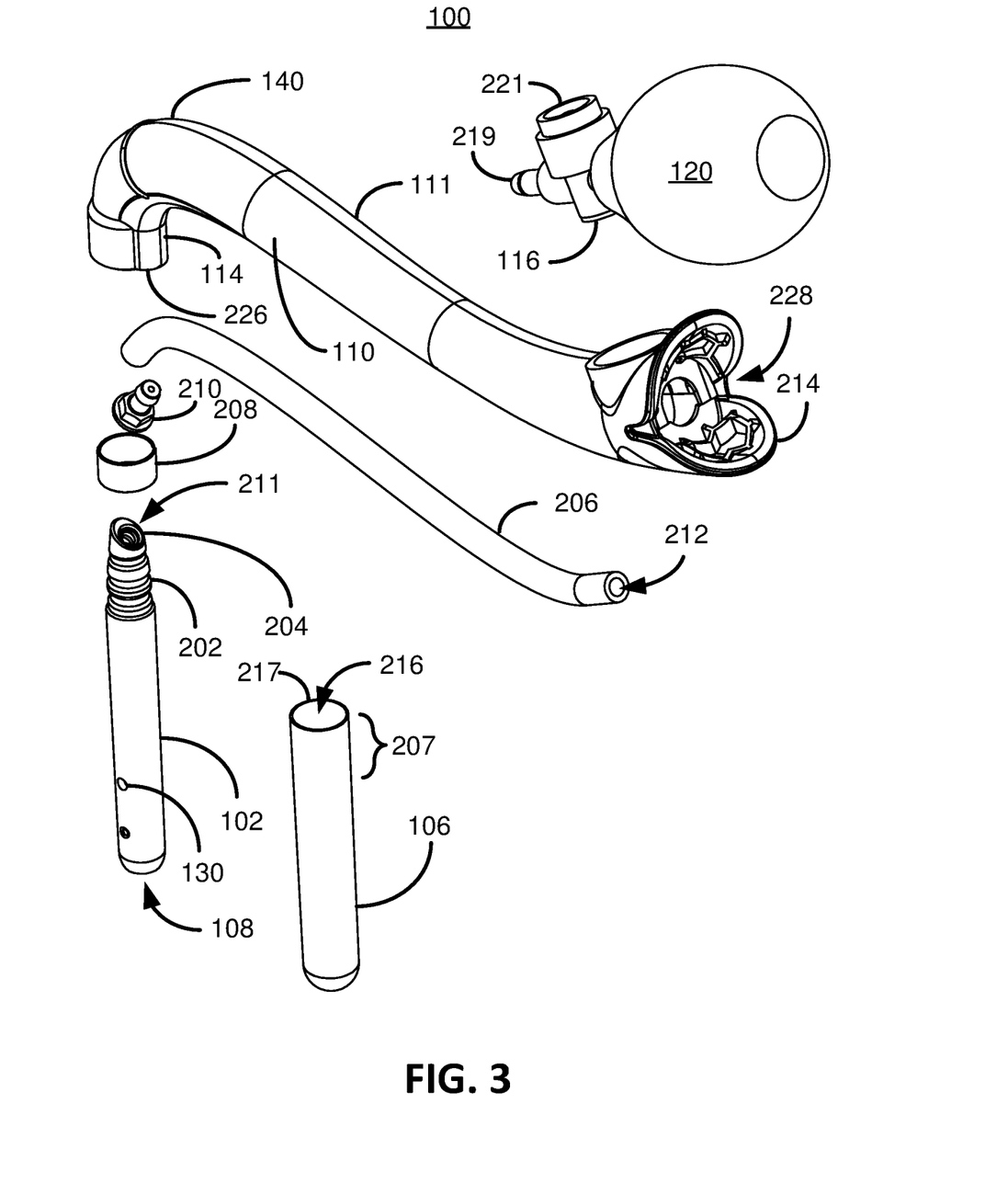
FIG. 3 illustratively depicts an exploded view of components that generally comprise the present rectocele device consistent with embodiments of the present invention.

FIG. 3 illustratively depicts an exploded view of components that generally comprise the present rectocele device 100 consistent with embodiments of the present invention. As shown, the bulb 120 is a flexible rubber squeeze bulb that when squeezed by a human hand forces air through the valve 116 and into the handle tube 206 that internally runs inside of the handle 110. The valve nipple 219 fits/cooperates with the opening 212 in the handle tube 206. The valve 116 channels air squeezed from the bulb 120 in one direction to the paddle 102 preventing backflow of air unless released by actuating/activating a valve release button 221. The bulb 120 and valve 116 fit in a receiving/accommodating opening 214 at the proximal end 228.

The handle 110 possesses a handle shaft 111 that transitions to a handle neck/bend 140. At the distal end of the handle 110 is a handle collar 114 configured to receive the paddle 102 cuff 208. In the present configuration, the proximal end of the paddle 102 fits over a connector 210 that can be pressed inside of the handle tube 206. There is an uninterrupted passageway 320 (shown in FIG. 4) formed between the proximal handle tube opening 212 and the paddle 102. A balloon 106 is configured to fit over the paddle 102. The paddle 102 is slid through the inflation outlet 216 defined by the balloon lip 217 until the balloon 106 essentially covers the paddle 102. The proximal balloon region 207 essentially covers the ringed contours 202 at the proximal end of the paddle 102. The cuff 208 fits/clamps over the proximal balloon region 207 thereby fixedly retaining the balloon 106 over the ringed contours 202 of the paddle 102. The cuff 208 prevents air from leaking through the inflation outlet 216 when engaged with the balloon and ringed contours 202. A skilled artisan will appreciate that there are a number of other clamping arrangements conceivable to fix the balloon 106 over the paddle 102 to function within the scope and spirit of the present invention after seeing the disclosed embodiment.

Figure 4:
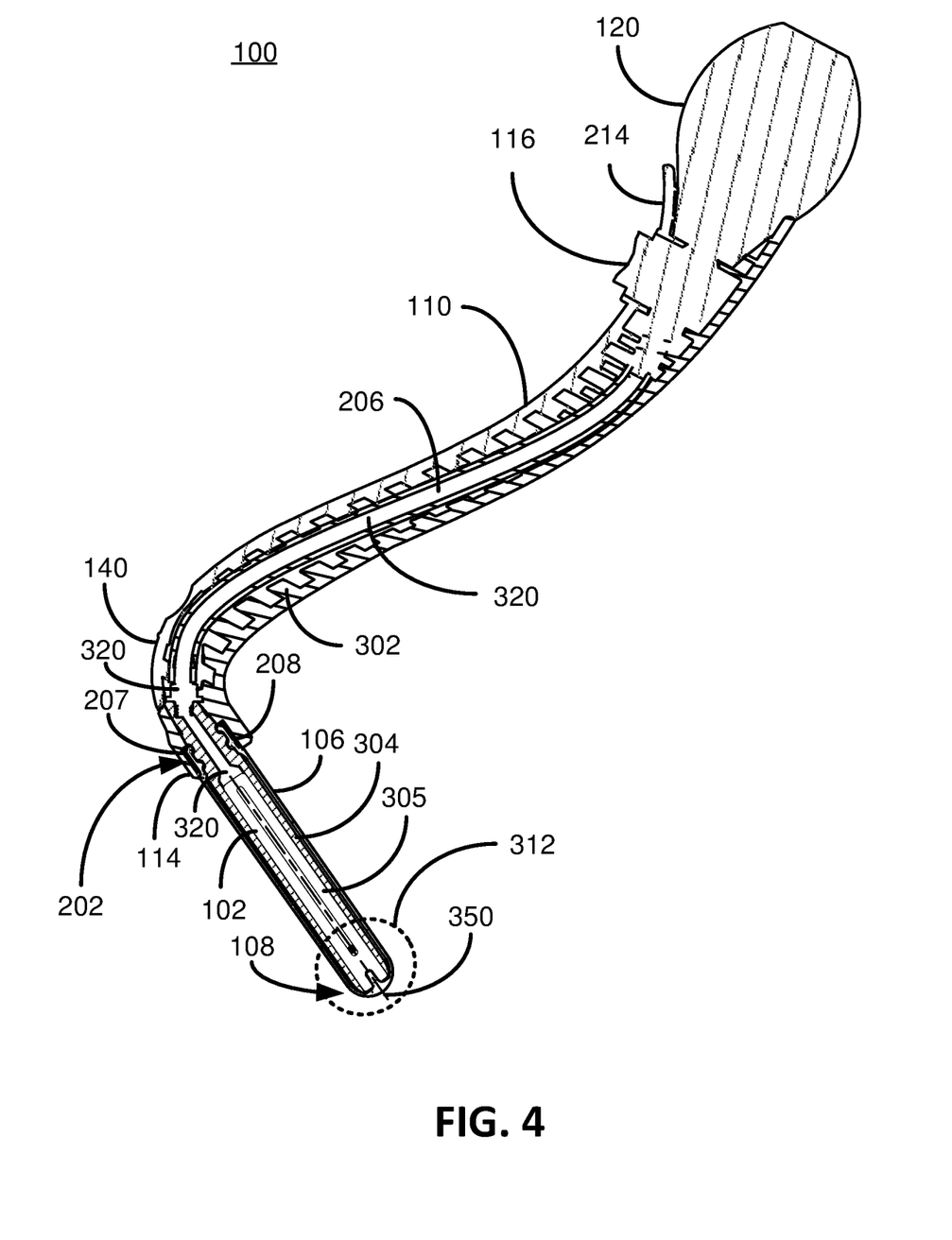
FIG. 4 illustratively depicts a cross-section side view drawing of a rectocele device embodiment consistent with embodiments of the present invention.

FIG. 4 illustratively depicts a cross-section side view drawing of a rectocele device embodiment consistent with embodiments of the present invention. As shown, there is an uninterrupted unidirectional passageway 320 between the proximal end of the rectocele handle one-way valve 116 and at least one exit aperture 130 (see FIG. 3). The at least one exit aperture 130 is in communication with the passageway 320. The term "in communication" as used here means that the at least one exit aperture 130 is actually part of the passageway 320 whereby air can freely flow through the at least one exit aperture 130 from the passageway 320 and into the balloon 106, and vice versa. The unidirectionality of the uninterrupted unidirectional passageway 320 is due to the one-way valve 116, which permits air squeezed (by hand) from the bulb 120 to go into the paddle 102/balloon 106 system, but not to escape from the balloon 106 unless desired. Hence, the pathway 320 extends from the bulb 120, through the one-way valve 116, through the rectocele handle 110, through the connector 210 and into the paddle 102, as shown. The one-way valve 116 can be physically actuated to open allowing air to flow out of the balloon 106 via the pathway 320 and into open air external to the rectocele device 100. Certain embodiments envision a push button release valve 221 through which pressurized air from the balloon 106 can escape through the valve 116 when the release valve 221 is actuated in an open position. For reference, the molded handle 110 possesses weight reducing/material reducing ribs 302. The handle 110 is intended to be grasped by a human hand during operation wherein the rectocele device 100 is used to manipulate a rectocele 4.

As further shown in FIG. 4, the proximal balloon region 207 is interposed between the cuff 208 and the ringed contours 202 of the paddle 102 thereby effectively sealing the inflation outlet 216 from releasing air from the balloon 106 when inflated. In certain embodiments, the cuff 208 clamps the proximal balloon region 207 against the ringed contours 202. The pathway 320 extends into the paddle 102 as shown by the space leading into the opening 211 at the distal end of the paddle 204. The paddle distal end 108, which in this case is covered with a balloon 106, is encircled by the dashed circle 312 to show in greater detail in FIGS. 5A-5C.

Figure 5A:
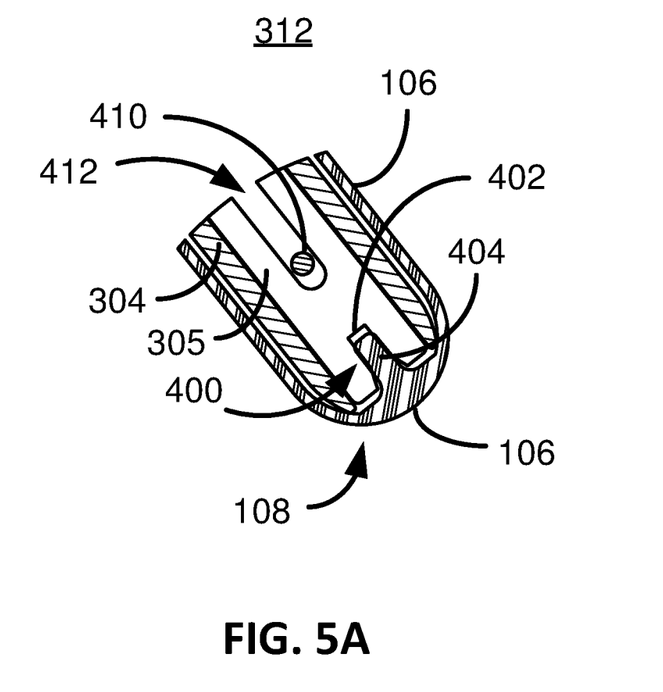
FIGS. 5A-5C are line drawings depicting a more detailed cross-section view of the distal end of a paddle and balloon embodiment consistent with embodiments of the present invention.

FIGS. 5A-5C are line drawings depicting a more detailed cross-section view of the distal end of a paddle 102 and balloon 106 embodiment consistent with embodiments of the present invention. FIG. 5A shows the distal end 108 of the paddle 102 and balloon 106 from the dashed circle 312 (as shown in FIG. 4). The balloon 106 essentially covers the piston housing 304, as discussed in detail in conjunction with FIGS. 3 and 4. The piston distal end 406 possesses a slot/recess 402 that receives or otherwise matingly engages 400 with an accommodating balloon protrusion 404, as shown. Certain embodiments envision the balloon protrusion 404 fixedly attaching to the piston distal end 406, such as by glue, pressure fit, adhesive, or other techniques that would be understood by those skilled in the art after the benefit of seeing this disclosure. The pin 410 is shown here for reference located in the piston slot 412.

Figure 5B:
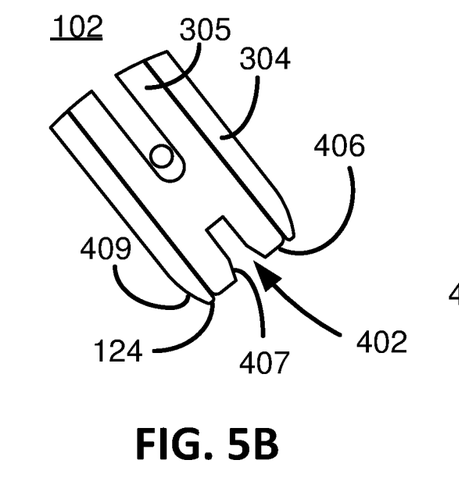

FIG. 5B depicts the distal end 108 of the cross-section view of the paddle 102 from the dashed line circle 312 (as shown in FIG. 4), consistent with embodiments of the present invention. In this embodiment, the piston 305 is in a fully retracted position that is fully inside of the piston housing 304. However, in other embodiments the piston 305 is at least partially outside of the piston housing 304 when in a fully retracted position. A fully retracted position is when the piston 305 is disposed in the piston housing 304 as far as the piston 305 will allow. With continued reference to the present embodiment, the piston distal end 406 is exposed at the piston through port 124 (i.e., the piston distal end 406 is viewable and accessible via the piston through port 124 at least when not covered by the balloon 106 or a sheath). The piston through port 124 can be circular in shape or some other shape, such as elliptical, angular or other. The piston 305 is free to move in and out of the piston through port 124 without obstruction so long as the piston 305 remains at least partially inside the piston housing 304, i.e., the piston 305 does not separate from the piston housing 304. Certain embodiments, not depicted here, envision the piston 305 being unconstrained and free to escape and separate from the piston housing 304. In the present embodiment, the piston housing distal end 409 is tapered to prevent a high stress point that would otherwise be created by a corner against the balloon 106. This embodiment depicts a chamfer 407 at the slot/recess 402 to more easily accommodate receiving the balloon protrusion 404.

Figure 5C:
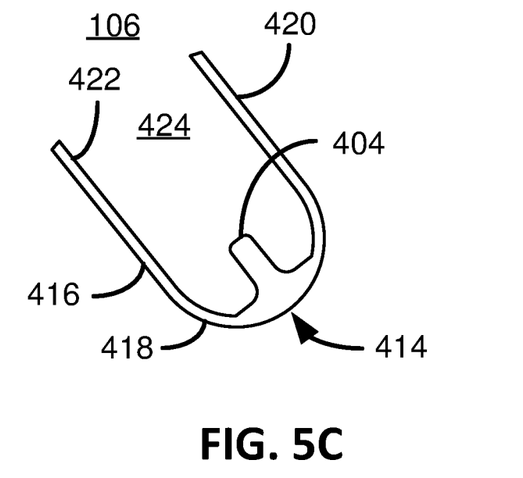

FIG. 5C depicts the distal end 108 of just the cross-section view of the balloon 106 from the dashed line circle 312 (as shown in FIG. 4), consistent with embodiments of the present invention. As shown, the balloon 106 is generally defined by an inside surface 422, an outside surface 420, a drip point 414 at the balloon distal end 418, cylindrical balloon side walls 416 extending towards a balloon lip 217, which defines the inflation outlet 216 (shown in FIG. 3) altogether defining a balloon interior 424. More specifically, the inside surface 422 covers the paddle mechanism 102, which includes the piston housing 304 and when extended, the piston 305. On the inside surface 422 at the drip point 414 is a balloon protrusion 404 extending towards the inflation outlet 216. The balloon protrusion 404 is configured to cooperate (matingly engage) with the slot/recess 402 at the distal end 406 of the piston 305 to essentially connect with the slot/recess 402. Certain embodiments envision the balloon protrusion 404 being adhered to, or fixedly attached to, the slot/recess 402. Other embodiments envision the balloon protrusion 404 being a post that fits into an accommodating posthole. Other embodiments envision the inside of the balloon not having a feature that connects with the distal tip 406 of the piston 305, rather the inside of the balloon adhering to the distal tip 106 by way of glue, tape, or some other means known to those skilled in the art. As discussed in more detail in connection with FIGS. 6A and 6B, the balloon 106 is configured to inflate when the balloon interior 424 is positively pressurized, typically with air. The word inflated as used herein does not necessarily mean to fully inflate, but is considered at least partially inflated, as well.

Figure 6A:
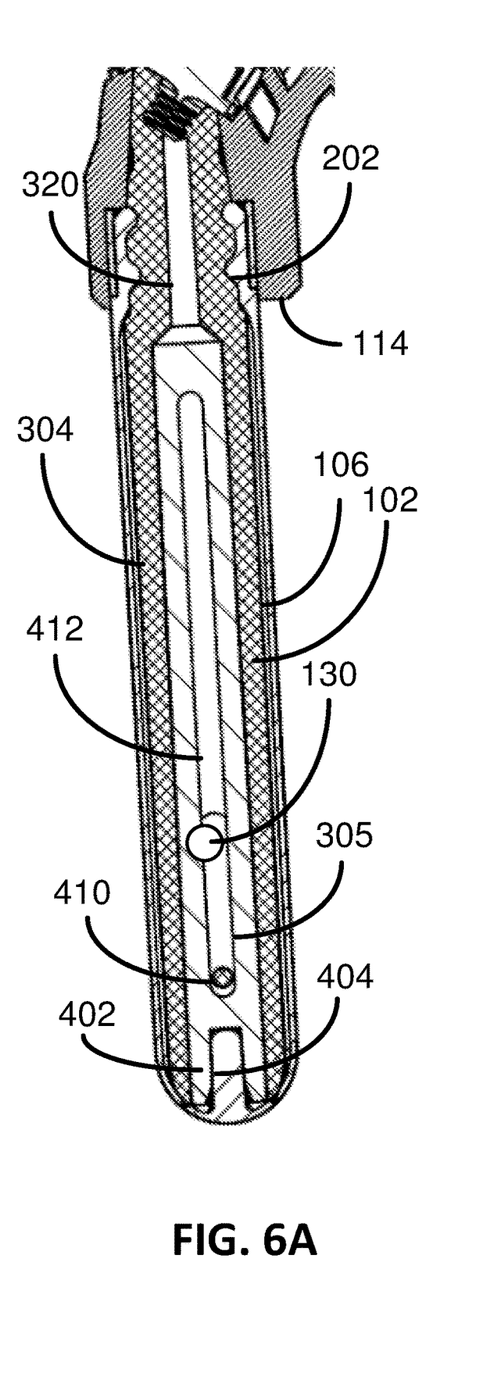
FIGS. 6A and 6B illustratively depict line drawings of cross-sectional views of the paddle and balloon when the rectocele device is in operation consistent with embodiments of the present invention.
Figure 6B:
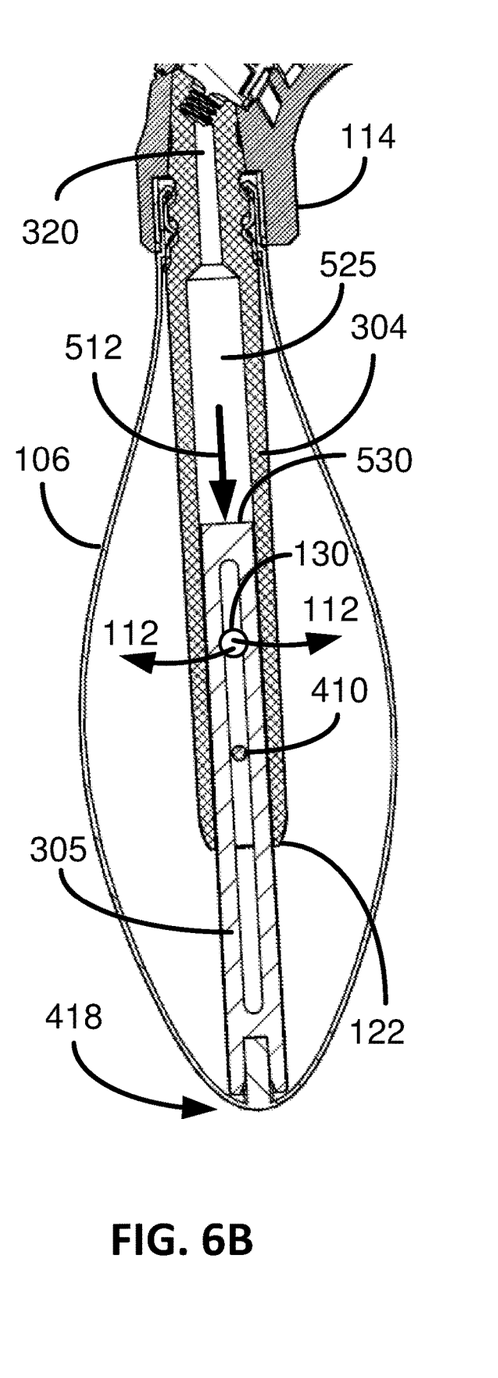

FIGS. 6A and 6B illustratively depict line drawings of cross-sectional views of the paddle and balloon when the rectocele device 100 is in operation consistent with embodiments of the present invention. As shown in FIG. 6A, the piston 305 is fully retracted in the piston housing 304, which in this embodiment (the piston 305) is essentially inside of the piston housing 304. The paddle 102, which essentially comprises the piston housing 304 and the piston 305, is essentially fully covered/encased by the balloon 106. The balloon 106 is attached to the handle collar 114 via the clamping action of the collar 208 compressing the balloon against the ringed contours 202. As a skilled artisan will appreciate after the benefit of reading the present disclosure, there are a number of optional ways to attach the proximal balloon region 207 to the distal handle end 226. In the present embodiment, the balloon 106 is fixedly engaged with the piston distal end 406 by way of the balloon protrusion 404 fixed/attached with the slot/recess 402. For reference, the at least one exit aperture 130, the pin 410 and slot 412 configuration and the passageway 320 are shown.

FIG. 6B illustratively depicts an example of positive pressurized air 112 flowing into the balloon interior 424 thereby inflating the balloon 106 consistent with embodiments of the present invention. As the balloon 106 inflates, the piston 305 extends outwardly from the piston housing 304 via the piston housing distal end 122. The pin 410 and slot 412 arrangement keep the piston 305 from rotating within the piston housing 304 as well as retaining the piston 305 to remain at least partially inside of the piston housing 304. Certain embodiments envision a component of the pressurized air 512 contributing to pushing the piston 305 partially out from the piston housing distal end 122. In other words, the balloon distal end 418 pulls the piston 305 from the piston housing 304 in addition to the component of the pressurized air 512 pushing on the piston top 530, which pushes the piston 305 from the piston housing 304. The newly created space 525 is an expanded part of passageway 320 showing the piston top 530 being pushed by the arrow 512. In this way, when the paddle 102 is vaginally 6 deployed, the piston 305 provides added stability to the inflated balloon 106.

Figure 7:
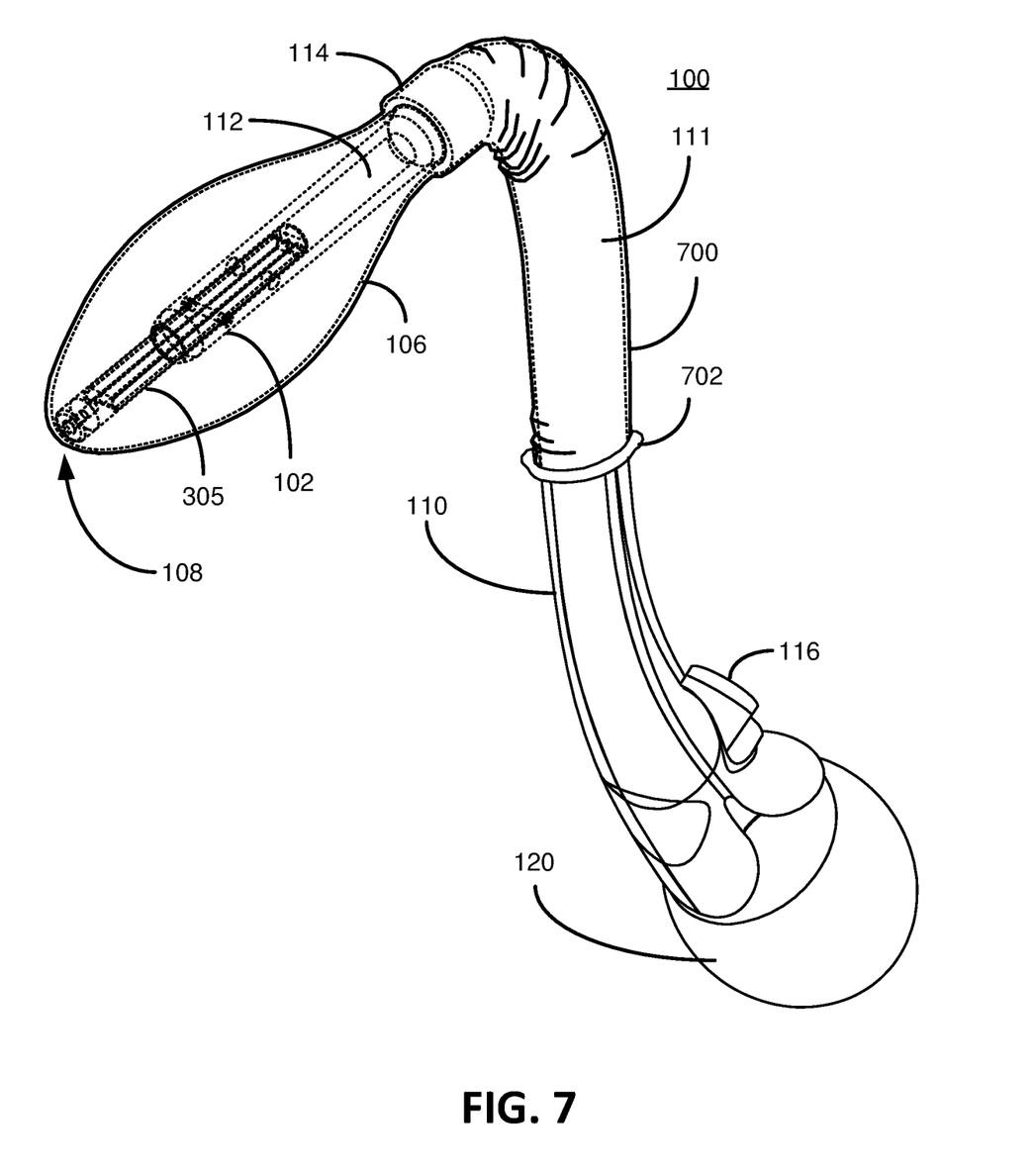
FIG. 7 illustratively depicts an embodiment of the rectocele device with a protective sheath covering the paddle and a portion of the handle consistent with embodiments of the present invention.

FIG. 7 illustratively depicts an embodiment of the rectocele device 100 with a protective sheath 700 covering the paddle 102 and a portion of the handle 110 consistent with embodiments of the present invention. As shown here, a protective sheath 700 is covering, or otherwise encapsulating, the balloon 106, paddle 102, the handle neck 140 and a portion of the handle shaft 111. The protective sheath 700 can be an elastic polymeric sheath (though other materials within the scope and spirit of the present invention are conceivable as understood by those skilled in the art) that conforms with the elements it covers but allows the balloon 106 and the piston 305 to freely move in order to perform their designated functions. In other words, the protective sheath 700 essentially does not impede or restrict the balloon 600 from expanding or the piston 305 from moving in and out of the piston housing 304, as depicted in FIG. 7. Hence, certain embodiments envision the protective sheath 700 being less than or equal to the elasticity of the balloon 106. The protective sheath 700 acts as a barrier between a vagina 6 and the rectocele device 100. In other words, the protective sheath 700 does not permit any biologic material present in a vagina 6 from coming in to contact with the area covered by the protective sheath 700. Because the balloon 106, the handle neck 140, and the portion of the handle shaft 111 do not come into direct contact with a vagina 6, they are essentially not soiled from bodily contamination. After use (i.e., when the rectocele is no longer inserted in a vagina 6), the protective sheath 700 can be pulled off of the portion of the handle shaft 111, the handle neck 140, and the balloon 106 covered paddle 102, and then discarded.

As shown, the elements of the rectocele device 100 inside of the protective sheath 700 are depicted as dashed lines to indicate that they are inside of the protective sheath 700. Further as shown, the protective sheath 700 covers and conforms to a portion of the handle shaft 111. In certain embodiments, the protective sheath 700 is made out of rubber and is essentially retained/held (by way of friction) to the handle shaft 111 without slipping off the rectocele device 100 during use. Some embodiments envision the flexible sheath elastically gripping the rectocele handle 110 when the elastic handle has a larger diameter than at least a portion of the elongated sheath cylinder 706 of the protective sheath 700 (see FIG. 8A). It is further envisioned in certain embodiments that the protective sheath 700 covers enough of the handle 110 for a person to at least partially grip the part of the protective sheath 700 that covers the handle 110. This provides additional measures to prevent the protective sheath 700 from slipping off the rectocele device 100 during use.

Figure 8A:
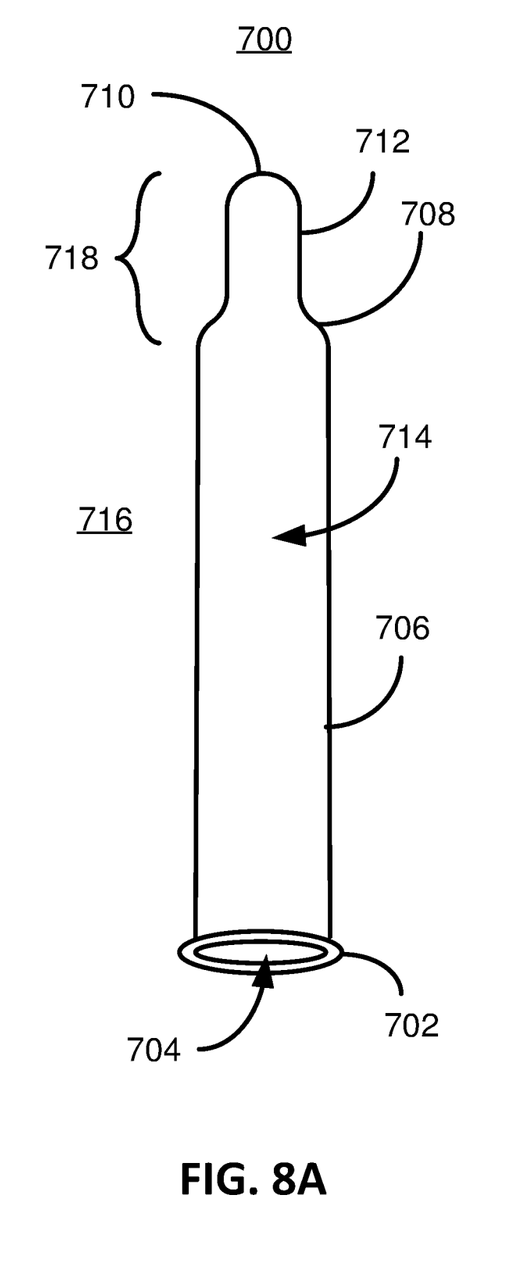
FIGS. 8A and 8B illustratively depict line drawings of a protective sheath embodiment unrolled and rolled consistent with embodiments of the present invention.
Figure 8B:
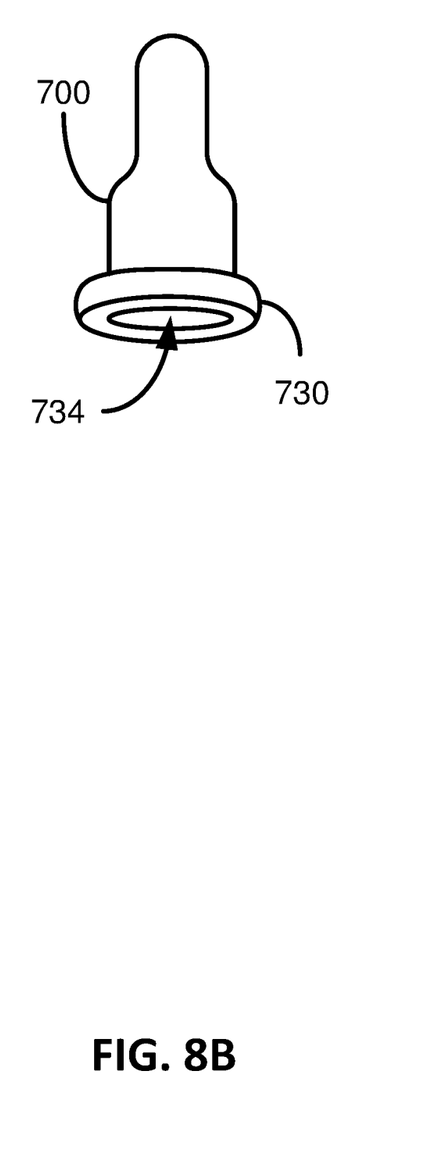

FIGS. 8A and 8B illustratively depict line drawings of a protective sheath embodiment unrolled and rolled consistent with embodiments of the present invention. As shown in FIG. 8A, the fundamental elements of the protective sheath 700 include a sheath apex 710 that extends along an elongated sheath cylinder 706, which terminates at a sheath lip 702. The sheath lip 702 defines a sheath entry port 704. The sheath 700 is similar to the balloon 106 in that a) the sheath entry port 704 is the sole opening, b) the protective sheath 700 can expand and contract, and c) the protective sheath 700 acts as a barrier between an internal environment 714 of the sheath 700 and the external world 716. In certain embodiments, the barrier is essentially capable of preventing the passage of material at an atomic level, such as air. In the present embodiment, the sheath distal region 718 of the protective sheath 700 is essentially defined by a smaller diameter sheath cylinder 712 that is tapered 708 from the elongated sheath cylinder 706, which terminates into the sheath apex 710. The geometry within the sheath distal region 718 can help facilitate air bubble release during manufacturing, which may cause defects in the impermeability of protective sheath 700. The distal end region 718 transitions to the elongated sheath cylinder 706 at an angle sufficient to cause air bubble release during manufacturing, that in some embodiments is approximately 45%, or could optionally be in a range that is between 40%-50%. Some embodiments envision the protective sheath 700 having a length defined as between the sheath lip 702 and the sheath apex 710, while other embodiments contemplate the sheath 700 being between 4 inches and 5 inches long. The wall thickness of the sheath 700 is between 5 mm and 15 mm, or approximately 10 mm in certain embodiments. Embodiments envision the elongated sheath cylinder 706 being about 0.65 inches in diameter, while other embodiments envision the range of between 0.60 inches and 0.70 inches. The smaller diameter sheath cylinder 712 is envisioned to be approximately 0.42 inches with an optional range of +/−0.5 inches. The spherical radius at the sheath apex 710 is envisioned to be approximately 0.21 inches with an optional range of +/−0.05 inches. FIG. 8B illustratively depicts the protective sheath 700 of FIG. 8A in a rolled up configuration. As shown in the rolled up configuration, a substantial portion of the elongated sheath cylinder 706 is rolled upon itself creating a roll cuff 730 that defines a roll sheath entry port 734. The roll sheath entry port 734 differs from the sheath entry port 704 only by way of the roll 730. In the present embodiment, the elongated sheath cylinder 706 is rolled over itself near the sheath distal region 718. However, certain embodiments envision the elongated sheath cylinder 706 being rolled up to the sheath distal region 718, while other embodiments envision the roll 730 being essentially all the way at the sheath apex 710.

Figures 9A, 9B:
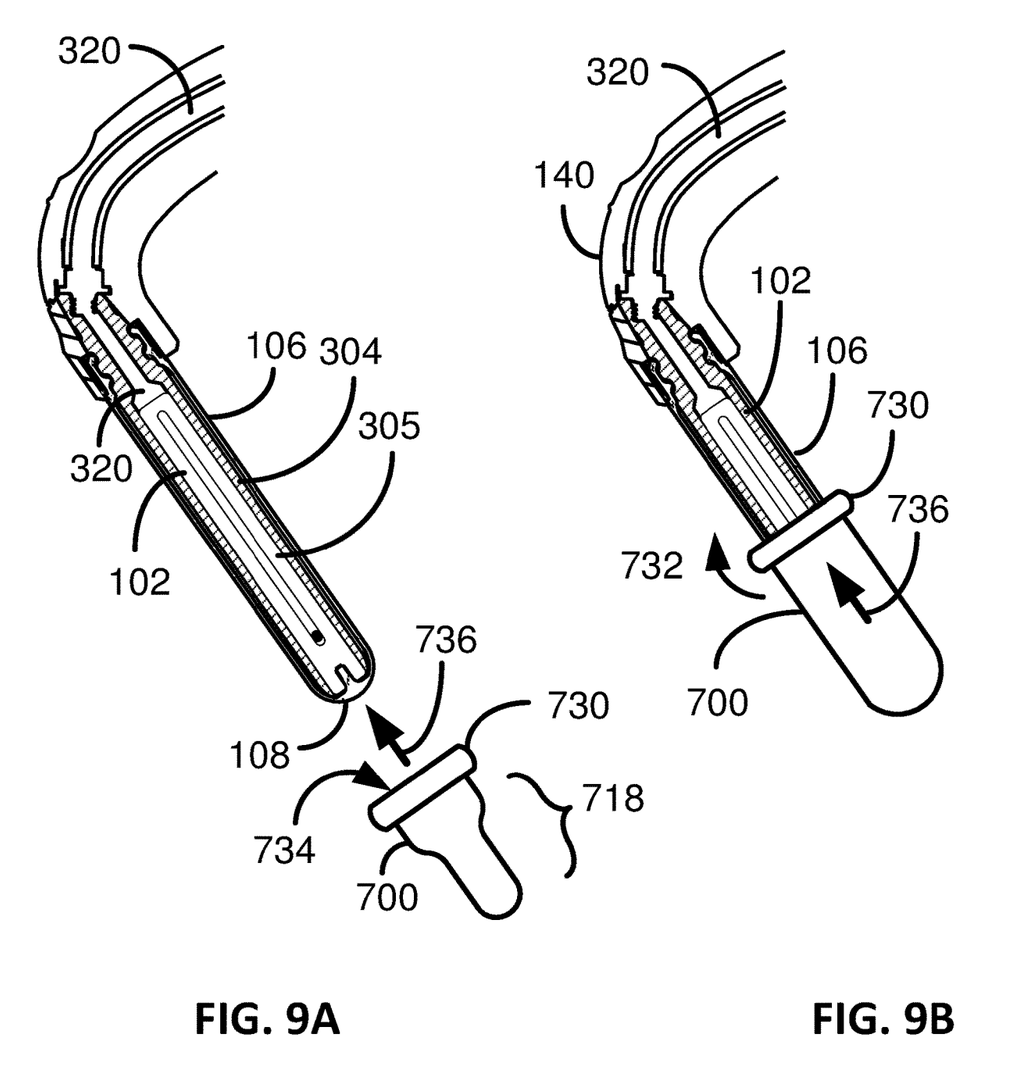
FIGS. 9A and 9B illustratively depict line drawings of a protective sheath being applied to a rectocele device consistent with embodiments of the present invention.

FIGS. 9A and 9B illustratively depict line drawings of a protective sheath being applied to a rectocele device 100 consistent with embodiments of the present invention. With respect to FIG. 9A, the protective sheath 700 is in a rolled up configuration, as shown in FIG. 8B, with the sheath roll entry port 734 interfacing the paddle distal end 108. A method of using the protective sheath 700 and a rolled up configuration can include a step for positioning (shown by arrow 736) the paddle distal end 108 at the flexible sheath entry port 704, or in this case, the sheath roll entry port 734. The next step is to move (shown by arrow 736) the vaginal paddle 102 into the flexible sheath entry port 704, which in this case is the roll entry port 734 as shown in FIG. 9B. FIG. 9B shows the protective sheath 700 partly on the paddle 102 and being unrolled 732 over the paddle 102. Hence, a step for putting the protective sheath 700 over the paddle 102 in this instance is the step of unrolling the protective sheath 700 over the balloon 106 covering the paddle 102 and over a portion of the rectocele handle 110 as depicted in FIG. 7. As previously mentioned, the protective sheath 700 can provide an impermeable cover protecting elements inside of the protective sheath 700. After the rectocele device 100 combined with the protective sheath 700 is used, the protective sheath 700 can be pulled off, rolled off, but either way, is taken off or otherwise separated from the rectocele device 100 and discarded/thrown away. The procedure can be repeated over and over again in an effort to keep the rectocele device from being unacceptably contaminated with biological contamination from inside of a vagina. Because a small amount of biological contamination may get on the rectocele device 100 due to the fact that the protective sheath 700 does not hermetically seal the entire rectocele device 100, it is considered an acceptable amount of biological contamination. An unacceptable amount of biological contamination is considered an amount of biological contamination that would get onto the balloon 106 and rectocele handle 110 if the protective sheath 700 was not there.

With the present description in mind, some embodiments of the present invention contemplate:

Embodiment 1: A rectocele device comprising: a rectocele handle 110 defined in part between a proximal handle end 228 and a distal handle end 226; a vaginal piston housing 304 extending from the distal handle end 226 and terminating at a piston housing distal end 122, a piston through port 124 located at the vaginal piston housing distal end 122; a piston 305 inside of the vaginal piston housing 304, the piston 305 possessing a piston distal end 406, the piston distal end 406 exposed at the piston through port 124, the piston 305 inseparable from the vaginal piston housing 304; an uninterrupted unidirectional passageway 320 extending through the rectocele handle 110 from the proximal handle end 228 through the distal handle end 226 and into the vaginal piston housing 304; and at least one exit aperture 130 extending through the vaginal piston housing 304, the at least one exit aperture 130 in communication with the passageway 320.

Embodiment 2: The rectocele device of embodiment 1 further comprising a balloon 106 essentially covering the vaginal piston housing 304, the balloon generally defined by an inside surface 422, an outside surface 420, a drip point 414 and a balloon lip 217, the balloon lip 217 defines and inflation outlet 216.

Embodiment 3: The rectocele device of embodiment 2 wherein the inside surface 422 is attached to the piston distal end 406 at the drip point 414.

Embodiment 4: The rectocele device of embodiment 2 wherein the inside surface 422 is attached to the piston distal end 406 at the drip point 414 via adhesive.

Embodiment 5: The rectocele device of embodiment 2 wherein the inside surface 422 at the drip point 414 possesses a protrusion 404 that is matingly engaged with an accommodating recess in the piston 305 at the piston distal end 406.

Embodiment 6: The rectocele device of embodiment 2 wherein a portion of the piston 305 is extended from the vaginal piston housing 304 via the piston through port 124 when the balloon 106 is inflated with pressurized air 112 received from the passageway 320.

Embodiment 7: The rectocele device of embodiment 6 further comprising an elastic bulb 120 in communication with the passageway 320 and attached to the proximal handle end 228, the pressurized air 112 is from the elastic bulb 120.

Embodiment 8: The rectocele device of embodiment 1 wherein the vaginal piston housing 304 is removably connected to the distal handle end 226.

Embodiment 9: The rectocele device of embodiment 2 wherein the balloon 106 extends from the distal handle end 226 when the balloon lip 217 is fixedly attached to the rectocele device 100.

Embodiment 10: A rectocele device comprising: a rectocele handle 110 defined in part by a proximal handle end 228 and a distal handle end 226; a vaginal piston housing 304 attached to the distal handle end 226 and terminating at a piston housing distal end 122, a piston through port 124 located at the vaginal piston housing distal end 122; a piston 305 that is at least in part confined inside of the vaginal piston housing 304, the piston 305 possessing a piston distal end 406, a piston through port 124 that accommodates movement of the piston 305, the vaginal piston housing 304 and the piston 305 are inseparable components of a vaginal paddle 102; an uninterrupted unidirectional passageway 320 extending through the rectocele handle 110 from the proximal handle end 228 through the distal handle end 226 and into the vaginal piston housing 304; and a balloon 106 essentially covering the vaginal piston housing 304, the balloon defined by an inside surface 422, an outside surface 420, a drip point 414 and a balloon lip 217, the balloon lip 217 defining an inflation outlet 216, the inside surface 422 in communication with the passageway 320.

Embodiment 11: The rectocele device of embodiment 10 further comprising at least one exit aperture 130 extending through the vaginal piston housing 304, the at least one exit aperture 130 in communication with the passageway 320.

Embodiment 12: The rectocele device of embodiment 10 means for attaching the inside surface 422 to the piston distal end 406 at the drip point 414.

Embodiment 13: The rectocele device of embodiment 10 wherein a portion of the piston 305 extends from the vaginal piston housing 304 via the piston through port 124 when the balloon 106 is inflated with pressurized air 112 received from an elastic bulb 120 in communication with the passageway 320, the elastic bulb 120 is attached to the proximal handle end 228.

Embodiment 14: The rectocele device of embodiment 10 wherein the vaginal piston housing 304 is attached to the distal handle end 226 by way of sleeve 208 that retains the balloon lip 217 over a ringed outer surface 202 on the vaginal piston housing 304.

Embodiment 15: A rectocele device comprising: a vaginal piston housing 304 possessing a proximal end 204 configured to connect to a distal handle end 226 of a rectocele handle 110 that is defined in part by a proximal handle end 228 and a distal handle end 226, the vaginal piston housing 304 terminating at a piston housing distal end 122, a piston through port 124 located at the vaginal piston housing distal end 122; a piston 305 that when in a first position is substantially inside of the vaginal piston housing 304, the piston 305 extended through the piston through port 124 in a position beyond the first position when in a second position, the piston 305 stays in cooperation with the vaginal piston housing 304 in both the first and the second positions; an inlet port 211 at the proximal end 204 and at least one outlet port 130 that passes through the vaginal piston housing 304; an uninterrupted unidirectional pathway 320 between the inlet port 211 and the outlet port 130; and the piston 305 terminating at a piston distal end 406, the piston distal end 406 adapted to confront a balloon interior 422.

Embodiment 16: The rectocele device of embodiment 15 further comprising an inlet port 211 at the proximal end 204 and at least one outlet port 130 that passes through the vaginal piston housing 304, and a pathway 320 between the inlet port 211 and the outlet port 130.

Embodiment 17: The rectocele device of embodiment 15 wherein the piston distal end 406 further comprises a slot configured to accommodate a protrusion 404 on the balloon interior 422.

Embodiment 18: The rectocele device of embodiment 15 wherein the vaginal piston housing 304 possesses a pin 410 that cooperates with a slot 412 that extends axially in the piston 305, the pin 410 keeps the piston 305 in cooperation with the vaginal piston housing 304 when the piston is in the second position.

Embodiment 19: The rectocele device of embodiment 15 wherein the vaginal piston housing 304 and the piston 305 comprise a vaginal paddle 102 that is configured to reside in a balloon 106.

Embodiment 20: The rectocele device of embodiment 19 wherein the balloon 106 is configured to pull the piston 305 in the second position when the balloon 106 is inflated, the balloon 106 is attached to the piston distal end 406 where the piston distal end 406 confronts the balloon interior 422.

Embodiment 21: The rectocele device of embodiment 16 wherein the balloon 106 is configured to be inflated by pressurized air passing through the pathway 320 and into the balloon 106 via the at least one outlet port 130, the balloon 106 is further configured to be constrained where the piston end 406 confronts the balloon interior 422 and where the vaginal piston housing 304 connects to the distal handle end 226.

Embodiment 22: A method for deploying a sheath over a rectocele paddle, the method comprising: providing a rectocele device 100 possessing a rectocele handle 110 defined in part by a proximal handle end 228 and a distal handle end 226, a vaginal piston housing 304 extending from the distal handle end 226 and terminating at a piston housing distal end 122, a piston through port 124 located at the vaginal piston housing distal end 122, and a piston 305 inside of the vaginal piston housing 304, the piston 305 possessing a piston distal end 406 that is attached to a balloon 106, the balloon 106 encasing the piston 305 and the vaginal piston housing 304; moving the vaginal piston housing distal end 122 into a flexible sheath entry port 704, the flexible sheath entry port 704 defined by a sheath roll 730; when the vaginal piston housing distal end 122 via the balloon 106 is in contact with an interior sheath apex, unrolling the sheath roll over the balloon 106 covered vaginal piston housing 304 and over a portion of the rectocele handle 110.

Embodiment 23: The method of embodiment 22 wherein the sheath impermeably covers the balloon 106 covered vaginal piston housing 304, and the portion of the rectocele handle 110.

Embodiment 24: The method of embodiment 23 wherein the portion of the rectocele handle 110 includes a handle neck 140 and part of a handle shaft 111.

Embodiment 25: The method of embodiment 22 wherein the sheath is elastic.

Embodiment 26: The method of embodiment 22 wherein the sheath comprises a distal end region that possesses a smaller diameter than the elongated sheath cylinder that terminates at a proximal inlet, the distal end region transitions to the elongated sheath cylinder at an angle.

Embodiment 27: The method of embodiment 26 wherein the angle is between 40 degrees and 50 degrees.

Embodiment 28: The method of embodiment 26 wherein the unrolled sheath is between 4 and 5 inches in length.

Embodiment 29: The method of embodiment 26 wherein the elongated sheath cylinder possesses a wall thickness that is between 5 mm and 15 mm.

Embodiment 30: The method of embodiment 26 wherein the elongated sheath cylinder is between 0.6 and 0.7 inches in diameter.

Embodiment 31: The method of embodiment 26 wherein the angle is sufficient to cause air bubble release during manufacturing.

Embodiment 32: The method of embodiment 22 wherein the elongated sheath cylinder is approximately 0.65 inches in diameter.

Embodiment 33: The method of embodiment 22 wherein the flexible sheath is less than or equal to the elasticity of the balloon 106.

Embodiment 34: The method of embodiment 22 further comprising the flexible sheath elastically gripping the rectocele handle 110 because the elastic handle has a larger diameter than at least a proximal region of the flexible sheath.

Embodiment 35: A method comprising: providing an elastic sheath that is rolled from a sheath entry port rim along a tubular sheath body towards a sheath tip forming a sheath roll, a sheath interior of the elastic sheath is viewable through the sheath roll; placing the roll and the sheath interior over a rectocele device 100 possessing a rectocele handle 110 defined in part by a proximal handle end 228 and a distal handle end 226, vaginal paddle 102 extending from the distal handle end 226, the vaginal paddle 102 comprising a vaginal piston housing 304 that terminates at a piston housing distal end 122, a piston through port 124 located at the vaginal piston housing distal end 122, and a piston 305 inside of the vaginal piston housing 304, the piston 305 possessing a piston distal end 406 that is attached to a balloon 106, the balloon 106 encasing the piston 305 and the vaginal piston housing 304; and covering the balloon 106 encased vaginal paddle 102 and at least a portion of the handle shaft 111 by unrolling the rolled elastic sheath over the balloon 106 encased vaginal paddle 102, over the distal handle end 226 and over the portion of the handle shaft 111.

Embodiment 36: The method of embodiment 35 further comprising inserting the covered balloon 106 encased vaginal paddle 102 into a vagina.

Embodiment 37: The method of embodiment 36 further comprising inflating the balloon 106 while the paddle 102 is inserted in the vagina, the elastic sheath does not restrict the inflating balloon 106.

Embodiment 38: The method of embodiment 35 wherein the elastic sheath seals any exposure between the vagina and the balloon 106 and the portion of the handle shaft 111.

Embodiment 39: A rectocele and sheath arrangement comprising: an impermeable sheath essentially defined by a tubular sheath body that extends from an entry port rim to a sheath tip, the impermeable sheath covering a vaginal paddle 102 that is encased in a balloon 106, the impermeable sheath further covering a portion of a rectocele handle 110, the rectocele handle 110 possessing a proximal handle end 228 and a distal handle end 226, the vaginal paddle 102 comprises a vaginal piston housing 304 attached to the distal handle end 226 and terminating at a piston housing distal end 122, and the vaginal paddle 102 further comprises a piston 305 that is at least in part confined inside of the vaginal piston housing 304, the piston 305 possessing a piston distal end 406, a piston through port 124 that accommodates movement of the piston 305.

The above embodiments are not intended to be limiting to the scope of the invention whatsoever because many more embodiments are easily conceived within the teachings and scope of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though the piston 305 concentrically extends from the piston housing 304, other embodiments contemplate a piston having a relationship with a piston housing that is non-concentric while still maintaining substantially the same functionality without departing from the scope and spirit of the present invention. Another example can include springs or other assisting mechanisms to help push the piston 305 out of the piston housing 304 or pull the piston 305 into the housing while still maintaining substantially the same functionality without departing from the scope and spirit of the present invention. Yet, other embodiments can include sheath shapes to accomplish the end result without departing from the scope and spirit of the present invention. The preferred embodiments described herein are directed to a rectocele device with some application as a cystocele device, which accordingly, is not intended for uses beyond the scope and spirit of addressing a rectocele or cystocele of a woman.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and as defined in the appended claims.

What is claimed is:

1. A method for deploying a sheath over a rectocele paddle, the method comprising:
    providing a rectocele device possessing a rectocele handle defined in part by a proximal handle end and a distal handle end, a vaginal piston housing extending from the distal handle end and terminating at a piston housing distal end, a piston through port located at the vaginal piston housing distal end, and a piston inside of the vaginal piston housing, the piston possessing a piston distal end that is attached to a balloon, the balloon encasing the piston and the vaginal piston housing;

moving the vaginal piston housing distal end into a flexible sheath entry port, the flexible sheath entry port defined by a sheath roll; and wherein when the vaginal piston housing distal end via the balloon is in contact with an interior sheath apex, unrolling the sheath roll over the balloon covered vaginal piston housing and over a portion of the rectocele handle.

2. The method of claim 1, wherein the sheath impermeably covers the balloon covered vaginal piston housing, and the portion of the rectocele handle.

3. The method of claim 1, wherein the portion of the rectocele handle includes a handle neck and part of a handle shaft.

4. The method of claim 1, wherein the sheath is elastic.

5. The method of claim 1, wherein the sheath comprises a sheath distal end region that possesses a smaller diameter than a sheath main body region that terminates at a proximal inlet, the sheath distal end region transitions to the sheath main body region at an angle.

6. The method of claim 5, wherein the angle is between 40 degrees and 50 degrees.

7. The method of claim 5, wherein the unrolled sheath is between 4 and 5 inches in length.

8. The method of claim 5, wherein the sheath main body region possesses a wall thickness that is between 5 mm and 15 mm.

9. The method of claim 5, wherein the sheath main body region is between 0.6 and 0.7 inches in diameter.

10. The method of claim 5, wherein the angle is sufficient to cause air bubble release during manufacturing.

11. The method of claim 1, wherein the sheath main body region is approximately 0.65 inches in diameter.

12. The method of claim 1, wherein the flexible sheath is less than or equal to the elasticity of the balloon.

13. The method of claim 1 further comprising the flexible sheath elastically gripping the rectocele handle because the elastic handle has a larger diameter than at least a proximal region of the flexible sheath.

14. A method comprising:

providing an elastic sheath that is rolled from a sheath entry port rim along a tubular sheath body towards a sheath tip forming a sheath roll, a sheath interior of the elastic sheath is viewable through the sheath roll;

placing the roll and the sheath interior over a rectocele device possessing a rectocele handle that is defined between a proximal handle end and a distal handle end, a vaginal paddle extending from the distal handle end, the vaginal paddle comprising a vaginal piston housing that terminates at a piston housing distal end, a piston through port located at the vaginal piston housing distal end, and a piston inside of the vaginal piston housing, the piston possessing a piston distal end that is attached to a balloon, the balloon encasing the piston and the vaginal piston housing; and covering the balloon encased vaginal paddle and at least a portion of the rectocele handle by unrolling the rolled elastic sheath over the balloon encased vaginal paddle, over the distal handle end and over the portion of the rectocele handle.

15. The method of claim 14 further comprising inserting the covered balloon encased vaginal paddle into a vagina.

16. The method of claim 15 further comprising inflating the balloon while the paddle is inserted in the vagina, wherein the elastic sheath does not restrict the inflating balloon.

17. The method of claim 14 wherein the elastic sheath seals any exposure between the vagina and the balloon and the portion of the rectocele handle.

18. A rectocele device and sheath arrangement comprising:

an impermeable sheath essentially defined by a tubular sheath body that extends from an entry port rim to a sheath tip, the impermeable sheath covering a vaginal paddle that is encased in a balloon, the impermeable sheath further covering a portion of a rectocele handle, the rectocele handle possessing a proximal handle end and a distal handle end, the vaginal paddle comprises a vaginal piston housing attached to the distal handle end and terminating at a piston housing distal end, and the vaginal paddle further comprises a piston that is at least in part confined inside of the vaginal piston housing, the piston possessing a piston distal end, a piston distal port that accommodates movement of the piston; and wherein when the balloon is inflated, the piston is jointly extended from the piston housing in mating engagement with the inflated balloon, and when the balloon is not inflated, the piston is essentially not extended from the piston housing.

19. The rectocele device and sheath arrangement of claim 18, wherein at least a portion of the impermeable sheath and the vaginal paddle are configured to be inserted in a vagina.

* * * * *